United States Patent [19]

Takahashi et al.

[11] Patent Number: 4,967,027
[45] Date of Patent: Oct. 30, 1990

[54] METHOD OF INHIBITING POLYMERIZATION OF STYRENES

[75] Inventors: Hideyuki Takahashi, Ibaraki; Shohei Suzuki, Mie; Tomohiko Takahama, Mie; Tadamichi Aoki, Mie; Yoshikazu Higaki, Mie, all of Japan; Karl Trukenbrod, Marl, Fed. Rep. of Germany

[73] Assignees: Mitsubishi Petrochemical Co., Ltd., Tokyo, Japan; Hüls Aktiengesellschaft, Marl, Fed. Rep. of Germany

[21] Appl. No.: 368,811

[22] Filed: Jun. 20, 1989

[51] Int. Cl.$^5$ ................................................. C07C 7/20
[52] U.S. Cl. ............................................ 585/5; 585/4
[58] Field of Search ........................................ 585/4, 5

[56] References Cited

U.S. PATENT DOCUMENTS 2,181,102 11/1939 Stoesser et al. .
4,237,336 12/1980 Fuga et al. ................................ 585/4
4,466,904 8/1984 Watson et al. .
4,468,343 8/1984 Butler et al. .
4,654,451 3/1987 Miller et al. ........................ 585/435

FOREIGN PATENT DOCUMENTS 56-86124 7/1981 Japan .
59-29624 2/1984 Japan .
2056481 3/1981 United Kingdom .

Primary Examiner—Curtis R. Davis
Attorney, Agent, or Firm—Oblon, Spivak, McClelland, Maier & Neustadt

[57] ABSTRACT

A method of inhibiting polymerization of styrenes is disclosed, comprising the process of jointly using nitrosophenols and p-tertiarybutyl catecol for composing the polymerization inhibiting agent usable during the distillation process of styrenes.

7 Claims, No Drawings

METHOD OF INHIBITING POLYMERIZATION OF STYRENES

FIELD OF THIS INVENTION

The present invention relates to a method of inhibiting polymerization of styrenes, more particularly, to a method of inhibiting polymerization applicable during the distillation process for separating and purifying styrenes.

BACKGROUND OF THIS INVENTION

High-purity styrenes usable for industries have been conventionally produced by separating and purifying a mixture generated from reaction by distillation. Styrenes, such as styrene, a substituted styrene, divinylbenzene, etc. have property of easily being polymerized, and thus, distillation is conventionally effected in the presence of a polymerization inhibiting agent.

A wide variety of compounds have been investigated for composing an agent of inhibiting the polymerization of the styrenes. However, of those conventional agents of inhibiting the polymerization of the styrenes available today, only nitrophenols and nitrosophenols have proved to be durable for industrial use in the distillation process. When sulfur is made available for example, environmental contamination arising from the burning of distilled residue is the critical problem. On the other hand, substituted alkylphenols, such as p-tertiarybutyl catechol, etc. have not enough ability to inhibit the polymerization of the styrenes at the distillation temperature when being used alone.

In addition, nitrophenols, such as 2,4-dinitrophenol, 2-methyl-4,6-dinitrophenol, 4-methyl-2,6-dinitrophenol, etc. have also been investigated. Nevertheless, any of these has mild activity to serve as the agent of inhibiting the polymerization of the styrenes, but instead, these respectively function as the polymerization retarding agent, and thus, any of these must be used with fairly high concentration. Considering toxicity incurring to human body, the nitrophenols cannot be determined as an ideal agent suited for inhibiting polymerization of the styrenes.

On the other hand, nitrosophenols have lower toxicity than that of the nitrophenols. Furthermore, according to JP-B-55-37974 (the term "JP-B" as used herein means an "examined Japanese patent publication"), in terms of the activity for inhibiting the polymerization of the styrenes, due to high reactivity of the nitrosophenols against an alkyl radical which causes the styrenes to generate thermal polymerization reaction and also due to high activity in inhibiting the polymerization, the nitrosophenols can effectively suppress the thermal polymerization of the styrenes.

Nevertheless, due to high reactivity of the nitrosophenols against the thermally generated alkyl radical, i.e., due to high activity for inhibiting the polymerization of the styrenes, after fully inhibiting the polymerization of the styrenes, a certain polymerization similar to the thermal polymerization in the absence of the inhibiting agent may be generated, and thus, in order to use it on the industrial basis, extreme precision is required for controlling the concentration of the polymerization inhibiting agent and the operating factors, such as temperature, pressure, etc. related to the distillation system.

SUMMARY OF THIS INVENTION

After following up concentrative study on the ideal agent of inhibiting the polymerization of the styrenes capable of generating high performance in inhibiting the polymerization and retarding the polymerization even after implementing the function to inhibit the polymerization, inventors have eventually achieved the present invention. Concretely, this invention provides the improved method of inhibiting the polymerization of the styrenes comprising the process of jointly using, the nitrosophenols and p-tertiarybutyl catechol for composing the agent of inhibiting the polymerization of the styrenes usable during the distillation process of the styrenes.

DETAILED DESCRIPTION OF THIS INVENTION

Based on the nitrosophenols having sufficient functional advantage in inhibiting the polymerization of the styrenes, inventors examined the effect of combining the nitrosophenols with other polymerization inhibiting agents. To our astonishment, a variety of compounds generated the negative effect. Sulfur, N-nitrosodiphenylamine, etc. generated the negative effect when being combined with the nitrosophenols. Phenothiazine proved to be totally ineffective.

On the other hand, when being combined with the nitrosophenols, p-tertiarybutyl catechol (hereinafter called p-TBC) distinctly showed the positive effect, although p-TBC proved to be insufficient in inhibiting the polymerization of the styrenes when being used alone. The improved performance in inhibiting the polymerization of the styrenes obviously exceeds the range of the additive property, and yet, it is likely that synergism is generated.

The term "styrenes" as used herein means the easily-polymerizable aromatic vinyl compounds, such as styrene, a substituted styrene, divinylbenzene, etc.

The nitrosophenols employed in this invention is represented by formula:

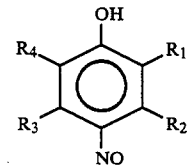

wherein $R_1$ through $R_4$ each represents hydrogen or a methyl group.

Concretely, examples of the above compound include 4-nitrosophenol, 2-methyl-4-nitrosophenol, 2,3,5-trimethyl-4-nitrosophenol, etc.

Any optional weight ratio is available for combining p-TBC with the nitrosophenols. However, it is desired that p-TBC be used in an amount of from 0.1 to 2.0, preferably from 0.2 to 1.2, part by weight based on 1.0 part by weight of the nitrosophenols. If both of these were used less than the recommended range, then the synergism lowers. Conversely, if both of these were used more than the recommended range, then, it will result in the economic disadvantage.

Normally, the styrenes, such as styrene for example, are generated by dehydrogenation from ethylbenzene. Reaction mainly generates a mixture of styrene and ethylbenzene, which are then separated and purified by the distillation process. Conventionally, the styrenes are distilled under reduced condition, at the temperature from 70 to 130° C. with about from 60 to 200 mmHg of the distillation pressure. Unless the occurrence of thermal polymerization is prevented in the above temperature range, large volume of polymer is generated.

The nitrosophenols are generally used in an amount of from about 50 to about 300, preferably from 50 to 150, ppm based on the amount of the styrenes.

If 100 ppm of the polymerization inhibiting agent embodied by this invention on the basis of the nitrosophenols fed to the distillation process were present against such polymerizable monomer, such as styrene, etc. then, the polymerization inhibiting agent can fully generate the own effect for inhibiting the polymerization of the styrenes. Furthermore, the polymerization inhibiting agent embodied by this invention can be fed to the distillation system through the following processes: First, the powdered nitrosophenols and p-TBC are fed in the blended or independent condition to the dissolving pool provided for the preparatory process. Then both are dissolved using crude styrene, etc. containing ethylbenzene, etc. Finally, the dissolved compound is fed to the distillation tower. Instead of crude styrene, etc., inert solvent capable of dissolving the polymerization inhibiting agent may also be used.

This invention has materialized an effective combination of the nitrosophenols having prominent effect and high activity for inhibiting the polymerization of the styrenes with p-TBC which does not provide sufficient effect for inhibiting the polymerization of the styrenes at the distilling temperature when being used alone. As a result, by effectively utilizing the prominent function of the nitrosophenols for inhibiting the polymerization of the styrenes, this invention provides an ideal polymerization inhibiting agent which securely prevents occurrence of the polymerization even after inhibiting the polymerization, and thus, the agent of inhibiting the polymerization of the styrenes embodied by this invention deserves attention of all the concerned. In addition, it renders effective service for stably and continuously operating those plants producing easily-polymerizable styrenes for a long while to come.

By presenting some example and comparative examples, the method of inhibiting the polymerization of the styrenes embodied by this invention is more concretely described below. It should be understood that the scope of this invention is by no means confined to the following preferred embodiment.

At the following example and comparative examples, the commercially procured styrene was washed with the alkaline aqueous solution to remove the polymerization inhibiting agent used for storage, and after washing it with pure water, the prepared styrene was distilled and purified immediately before starting the experiments.

EXAMPLE

First, each 100 ppm of 2-methyl-4-nitrosophenol and p-tertiarybutyl catechol were added to the purified styrene, and then, considering the styrene distillation condition, it was determined that the tests be conducted at 110° C.

Under argon atmosphere, the blending bath temperature was raised to 110 ± 0.5° C. and the blended material was continuously stirred. Then, the stirred material was sampled from time to time, and then the sampled material was analyzed by means of gel permeation chromatography (GPC) to eventually obtain the proportion of polymer in the styrene monomer (% by weight). The result is shown in Table 1.

COMPARATIVE EXAMPLE 1

The same procedure as for the above example was repeated except for the addition of 100 ppm of p-TBC to the purified styrene without adding 2-methyl-4-nitrosophenol. The test resulted in the generation of excessive volume of polymer, and as a result, after two hours are past, the proportion of polymer could not be eventually obtained. Test result is also shown in Table 1.

COMPARATIVE EXAMPLE 2

The same procedure as for the above example was repeated except for the addition of 100 ppm of 2-methyl-4-nitrosophenol to the purified styrene without adding p-TBC. The result is also shown in Table 1.

COMPARATIVE EXAMPLE 3

The same procedure as for the above example was repeated except for adding 600 ppm of sulfur to the purified styrene instead of 100 ppm of p-TBC. The result is also shown in Table 1.

COMPARATIVE EXAMPLE 4

The same procedure as for the above example was repeated except for adding 200 ppm of phenothiazine to the purified styrene instead of 100 ppm of p-TBC. The result is also shown in Table 1.

COMPARATIVE EXAMPLE 5

The same procedure as for the above example was repeated except for adding 300 ppm of N-nitrosodiphenylamine (NDPA) to the purified styrene instead of 100 ppm of p-TBC. The result is also shown in Table 1.

TABLE 1

|  | Combination of polymerization inhibiting agent | Proportion of generated polymer (% by weight) | | | |
| --- | --- | --- | --- | --- | --- |
|  |  | 1 hour | 2 hours | 3 hours | 4 hours |
| Example | Each 100 ppm of 2-methyl-4-nitrosophenol and p-TBC | 0.0 | 0.13 | 0.25 | 0.69 |
| Comparative Example 1 | 100 ppm of p-TBC | 2.0 | (Measurement impossible) | (Measurement impossible) | (Measurement impossible) |
| Comparative Example 2 | 100 ppm of 2-methyl-4-nitrosophenol | 0.0 | 0.19 | 0.42 | 1.29 |
| Comparative Example 3 | 100 ppm of 2-methyl-4-nitrosophenol and 600 ppm of sulfur | 0.1 | 1.30 | 2.69 | 4.09 |
| Comparative Example 4 | 100 ppm of 2-methyl-4-nitrosophenol and 200 ppm of phenothiazine | 0.0 | 0.20 | 0.41 | 1.22 |
| Comparative | 100 ppm of 2-methyl-4- | 0.1 | 1.27 | 2.51 | 3.81 |

TABLE 1-continued

| | Combination of polymerization inhibiting agent | Proportion of generated polymer (% by weight) | | | |
|---|---|---|---|---|---|
| | | 1 hour | 2 hours | 3 hours | 4 hours |
| Example 5 | nitrosophenol and 300 ppm of NDPA | | | | |

While this invention has been described in detail and with reference to specific embodiments thereof, it will be apparent to one skilled in the art that various changes and modifications can be made therein without departing from the spirit and scope thereof.

What is claimed is:

1. A method of inhibiting polymerization of styrenes comprising the process of jointly using nitrosophenols and p-tertiarybutyl catechol for composing the polymerization inhibiting agent usable during the distillation process of styrenes.

2. The method as claimed in claim 1, wherein said styrenes are selected from the group consisting of styrene, a substituted styrene and divinylbenzene.

3. The method as claimed in claim 1, wherein said nitrosophenols are represented by formula:

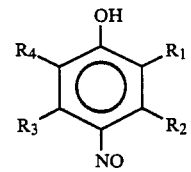

wherein $R_1$ through $R_4$ each represents hydrogen or a methyl group.

4. The method as claimed in claim 3, wherein said nitrosophenols are selected from the group consisting of 4-nitrosophenol, 2-methyl-4-nitrosophenol and 2,3,5-trimethyl-4-nitrosophenol.

5. The method as claimed in claim 1, wherein p-tertiarybutyl catechol is used in an amount of from 0.1 to 2.0 parts by weight based on 1.0 part by weight of the nitrosophenols.

6. The method as claimed in claim 1, wherein 50 to 300 ppm of said nitrosophenols are present against the styrenes.

7. The method as claimed in claim 1, wherein the styrenes are distilled at the temperature from 70 to 130° C.